(12) United States Patent
Lui

(10) Patent No.: US 7,931,938 B2
(45) Date of Patent: Apr. 26, 2011

(54) DIAMOND-LIKE CARBON-COATED CELL CULTURE SUBSTRATES

(75) Inventor: Ge Ming Lui, Honolulu, HI (US)

(73) Assignee: Cellular Bioengineering, Inc., Honolulu, HI (US)

( * ) Notice: Subject to any disclaimer, the term of this patent is extended or adjusted under 35 U.S.C. 154(b) by 1017 days.

(21) Appl. No.: 10/575,247

(22) PCT Filed: Oct. 8, 2004

(86) PCT No.: PCT/US2004/033194
§ 371 (c)(1),
(2), (4) Date: Apr. 13, 2007

(87) PCT Pub. No.: WO2005/037985
PCT Pub. Date: Apr. 28, 2005

(65) Prior Publication Data
US 2007/0274961 A1    Nov. 29, 2007

Related U.S. Application Data

(60) Provisional application No. 60/510,348, filed on Oct. 10, 2003, provisional application No. 60/510,358, filed on Oct. 10, 2003.

(51) Int. Cl.
*C23C 16/26* (2006.01)
(52) U.S. Cl. .............. 427/249.1; 427/248.1; 435/402; 435/395
(58) Field of Classification Search .................. None
See application file for complete search history.

(56) References Cited

U.S. PATENT DOCUMENTS

| 5,324,591 | A | 6/1994 | Georger, Jr. et al. | |
| 5,449,383 | A | 9/1995 | Chatelier et al. | |
| 2004/0219184 | A1* | 11/2004 | Brown et al. | 424/423 |

FOREIGN PATENT DOCUMENTS

| WO | WO 99/25396 A | 5/1999 |
| WO | WO 01/43790 * | 6/2001 |

OTHER PUBLICATIONS

Ignatius et al, "Bioactive surface coatings for nanoscale instruments: Effects on CNS neurons" J Biomed Mater Res, 1998, vol. 40, pp. 264-274.*
Steffen et al, Surface and Interface Analysis, 2000, vol. 19, p. 386-391.*
Lu et al., "Diamond-Like Carbon as Biological Compatible Material for Cell Culture and Medical Application", Bio-Medical Materials and Engineering, vol. 3, No. 4, pp. 223-228, 1993.

* cited by examiner

*Primary Examiner* — Allison M Ford
(74) *Attorney, Agent, or Firm* — Leydig, Voit & Mayer, Ltd.

(57) ABSTRACT

This present invention describes a method of coating a polymer surface with diamond-like carbon (DLC) to render it useful as a carrier for cells derived from neural crest origin, preferable neuronal cells that form dendrites. The biopolymer to be coated with the DLC will include biodegradable polymers and other implantable biopolymers to act as a carrier system for cell transplantation into the various parts of the body, including the brain, the eye, the central and peripheral nervous system, the lung, the liver, the spleen, the kidney, and the bone and cartilage. The biopolymer can be in sheet form or microparticle form, and can be imbedded with, or incorporated into during its synthesis, attachment or growth promoting reagents to enhance and support neuraonal call attachment and growth. This coating method can also augment other coating agents such as extracellular matrix (ECM) secreted by cultured bovine corneal endothelial cells, as well as adhesive molecules such as fibronectin, laminin, and RGDS. The coating step can be a sequential process where the DLC layer will be added on top of an ECM coated surface or an attachment factor coated surface.

23 Claims, No Drawings

DIAMOND-LIKE CARBON-COATED CELL CULTURE SUBSTRATES

This patent application is a nationalization of PCT/US04/033194 filed Oct. 8, 2004 which claims priority to U.S. patent application Ser. Nos. 60/510,358 filed Oct. 10, 2003; and 60/510,348 filed Oct. 10, 2003, and both are incorporated by reference herein as set forth in its entirety.

BACKGROUND OF THE INVENTION

1. Field of Invention

This invention relates generally to improved methods for growing various mammalian cells in vitro using cell culturing methods and novel cell culture surface compositions and methods of application.

2. Description of Prior Art

Cell transplantation has been proposed as an alternative for total organ replacement for a variety of therapeutic needs, including treatment of diseases in the eye, brain, liver, skin, cartilage, and blood vessels. See, for example, J P Vacanti et al., J. Pediat. Surg., Vol. 23, 1988, pp. 3-9; P Aebischer et al., Brain Res. Vol. 488, 1998, pp. 364-368; C B Weinberg and E. Bell, Science, Vol. 231, 1986 pp. 397-400; I V Yannas, Collagen III, M E Nimni, ed., CRC Press, Boca Raton, 1988; G L Bumgardner et al., Hepatology, Vol. 8, 1988, pp. 1158-1161; A M Sun et al., Appl. Bioch. Biotech., Vol. 10, 1984, pp. 87-99; A A Demetriou et al., Proc. Nat. Acad. Sci. USA, Vol. 83, 1986, pp. 7475-7479; W T Green Jr., Clin. Orth. Rel. Res., Vol 124. 1977, pp. 237-250; C A Vacanti et al., J. Plas. Reconstr. Surg., 1991; 88:753-9; P A Lucas et al., J. Biomed. Mat. Res., Vol. 24, 1990, pp. 901-911. The ability to create human cell lines in tissue culture will enhance the prospect of cell transplantation as a therapeutic mode to restore lost tissue function. It is especially vital to be able to create human cultured cell lines from tissues of the neural crest, since tissues or organs derived from that origin cannot usually repair itself from damage after an individual reaches adulthood.

Conventional tissue culture lab wares useful in growing cells in vitro, are usually coated with a negative charge to enhance the attachment and sometimes proliferation of mammalian cells in culture. However, traditionally it has been most difficult to achieve a satisfactory attachment, maintenance, and propagation of mammalian neuronal cells with the conventional tissue culture surfaces. Improvements have been made by adding layers of collagen gel or depositing an extracellular matrix secreted by rat EHS tumor cells onto the tissue culture plates and dishes to facilitate neural cell attachment and proliferation. These techniques, however, are hindered by the shortcoming that the material has to be layered on the culture surfaces shortly before the cells are seeded.

The use of a biopolymer carrier to support the attachment, growth, and eventually as a vehicle to carrying the cells during transplantation is vital to the success of cell replacement therapy, particularly in the brain and the back of the eye, where cells derived from the neural crest origin is often damaged during the aging process. There are seven general classes of biopolymers: polynucleotides, polyamides, polysaccharides, polyisoprenes, lignin, polyphosphate and polyhydroxyalkanoates. See for example, U.S. Pat. No. 6,495,152. Biopolymers range from collagen IV to polyorganosiloxane compositions in which the surface is embedded with carbon particles, or is treated with a primary amine and optional peptide, or is co-cured with a primary amine- or carboxyl-containing silane or siloxane, (U.S. Pat. No. 4,822,741), or for example, other modified collagens are known (U.S. Pat. No. 6,676,969) that comprise natural cartilage material which has been subjected to defatting and other treatment, leaving the collagen II material together with glycosaminoglycans, or alternatively fibers of purified collagen II may be mixed with glycosaminoglycans and any other required additives. Such additional additives may, for example, include chondronectin or anchorin II to assist attachment of the chrondocytes to the collagen II fibers and growth factors such as cartilage inducing factor (CIF), insulin-like growth factor (IGF) and transforming growth factor (TGFβ).

Until the advent of the present invention, it was not possible to culture mammalian or human neuronal tissues from the neural crest or individual neurons and get them to grow and divide in vitro.

SUMMARY OF THE INVENTION

One aspect of the present invention is the disclosure of methods of coating tissue culture lab ware with a stable layer of carbon plasma, most preferably the DLC that can enhance the attachment and growth of neuronal cells, and can provide a ready supply of apparatus for successful the tissue culture of these cell types.

Human or mammalian cells from the neural crest origin or neurons in particular, are known to exhibit two difficult behaviors. One is that they do not usually replicate in vivo or under tissue culture conditions, and secondly they do not attach very well to conventional cell culture surfaces. By coating a surface with carbon plasma, known as diamond-like carbon (DLC), the inventors have found that neurons will readily attach to the culture surface and exhibit a proliferation response.

The mechanical and tribological properties of DLC films (friction coefficient around 0.1 in air, hardness up to about 80 GPa, and elastic modulus approaching 600 GPa) are very close to those of diamond. Moreover, these films are chemically inert in most aggressive environments, and may be deposited with densities approaching that of diamond. However, in contrast to carbon vapor deposition, diamond, DLC films are routinely produced at room temperature, which makes them particularly attractive for applications where the substrate cannot experience elevated temperatures.

The present invention discloses the deposition of a DLC coat onto a biopolymer surface, which in turn will support the attachment and growth of human and mammalian neurons, as well as other cell types originating from the neural crest.

An object of the present invention is to create a specialized tissue culture platforms for the growth and maintenance of neuronal cells and cells of neural crest origin in vitro for the purpose of propagation of cell lines and performing experiments. The DLC coated products of the present invention include tissue culture dishes, flasks, slides, filter chambers, polymer and glass beads, sheets, and blocks. The coating can be deposited onto plastic, glass, synthetic and natural biopolymers, and metal. The DLC coat can be added on top of other types of coating such as extracellular matrix (ECM) secreted by cultured bovine corneal endothelial cells, adhesive molecule coating and growth factor coating to generate an improved product for specific human and mammalian cell growth.

In addition, the biopolymer used in the present invention, can be of natural or synthetic in origin. Natural biopolymers comprise collagen and other well known polymeric substances. For synthetic polymers, they can be acrylic and derivatives or copolymers such as polymethyl methacrylate, poly-N-isopropylacrylamide or poly-2-hydroxymethacrylate, polyvinyl alcohols and derivatives and copolymers. The biopolymer can either be a thin sheet or in microparticle form. To improve the growth supporting properties of the biopolymer, attachment or growth promoting factors can be embedded or incorporated into its composition during synthesis. Furthermore, a three dimensional growth medium suitable for supporting the growth and replication of neural cells comprising of a semi-solid biopolymer can also be coated with DLC to enhance its capability to support neuronal growth and maintenance. The biopolymer can also be comprised of chitosan or sodium alginate "may polymer" as well.

These and other objects of the invention, as well as many of the attendant advantages thereof, will become more readily apparent when reference is made to the following detailed description of the preferred embodiments.

DETAILED DESCRIPTION AND PREFERRED EMBODIMENTS

In describing a preferred embodiment of the invention specific terminology will be resorted to for the sake of clarity. However, the invention is not intended to be limited to the specific terms so selected, and it is to be understood that each specific term includes all technical equivalents which operate in a similar manner to accomplish a similar purpose.

The methods described in the present invention will allow the coating of a polymer surface with DLC and similar coatings to render it useful as a carrier for cells derived from neural crest origin. The biopolymer can be a biodegradable moiety. The biopolymer can either be in the form of a thin sheet, in microparticle form, or as a semi-solid block. The biopolymer is coated with by using a plasma gun which will deposit a thin layer of carbon plasma with the thickness of 200 to 400 Å on to the intended culture surface.

Similar to diamond-like carbon (DLC) coating, amorphous carbon nitride (C—N) films can be extremely hard and wear-resistant. They may serve as candidates for the solution to the problem of aseptic loosening of total hip replacements. It has been reported by Du et al., that morphological behavior of osteoblasts on silicon, DLC-coated silicon and amorphous C—N film-deposited silicon in organ culture was investigated by scanning electron microscopy. Cells on the silicon wafers were able to attach, but were unable to follow this attachment with spreading. In contrast, the cells attached, spread and proliferated on the DLC coatings and amorphous C—N films without apparent impairment of cell physiology. The morphological development of cells on the coatings and films was similar to that of cells in the control. The results support the biocompatibility of DLC coating and are encouraging for the potential biomedical applications of amorphous C-N films in the present invention (C. Du et al., Biomaterials. 1998 April-May; 19(7-9):651-8.

The DLC Coating Process is as Follows:

The plasma equipment consists of a vacuum arc plasma gun manufactured by Lawrence Berkeley National Laboratory, Berkeley, Calif., that is operated in repetitively-pulsed mode so as to minimize high electrical power and thermal load concerns. The fitted with a carbon cathode, the plasma gun forms a dense plume of pure carbon plasma with a directed streaming energy of about 20 eV. The plasma is injected into a 90° magnetic filter (bent solenoid) so as to remove any particulate material from the cathode, and then transported through a large permanent magnet multipore configuration that serves to flatten the radial plasma profile; in this way the carbon plasma deposition is caused to be spatially homogenous over a large deposition area.

To yet further enhance the film uniformity, the substrate(s) to be DLC coated are positioned on a slowly rotating disk, thus removing and azimuthal inhomogeneity. The apparatus described was used to form DLC films of about 2 to 4000 Å thick, preferably about 200-400 Å thick.

To improve the ability of the biopolymer in supporting cell growth or attachment, an attachment mixture comprising of one or more of the following will be embedded or incorporated into its composition during synthesis: fibronectin at concentrations ranging from 1 µg to 500 µg/ml of polymer gel, laminin at concentrations ranging from 1 µg to 500 µg/ml of polymer gel, RGDS at concentrations ranging from 0.1 µg to 100 µg/ml of polymer gel, bFGF conjugated with polycarbophil at concentrations ranging from 1 ng to 500 ng/ml of polymer gel, EGF conjugated with polycarbophil in concentrations ranging from 10 ng to 1000 ng/ml of polymer gel, NGF at concentrations of ranging from 1 ng to 1000 ng/ml of the polymer gel and heparin sulfate at concentrations ranging from 1 µg to 500 µg/ml of polymer gel.

In the thin sheet or microparticle forms, the coated biopolymer, in a preferred embodiment, is used as a carrier for neural cell growth and as a vehicle for cell delivery during a cell transplantation procedure. The semi-solid polymer block form can be used as a neural cell maintenance device in coupling with an integrated circuit chip or a CCD chip to function as a neural stimulation detector. The coated surface can be further improved by coating with an extracellular matrix deposited by cultured bovine corneal endothelial cells and then subsequently overlaid with a DLC coating.

Example 1

Coating a Biopolymer in the Form of a Sheet with DLC

The biopolymer sheets can be any dimension, preferably about 2 cm×2 cm of the present invention are fixed to a rotating disk which is in turn set up in the DLC coating chamber on top of a slowly rotating motor. The plasma equipment will generate a dense plume of pure carbon plasma via an ejecting gun with a directed streaming energy of about 20 eV. The plasma is injected into a 90° magnetic filter to remove any particulate material to form a high quality, hydrogen free diamond-like carbon. When transported through a large permanent magnet multipore configuration that serves to flatten the radial plasma profile, a carbon plasma deposition will be spatially homogenous over a large deposition area. As the carbon plasma plume approaches the slowly rotating disk holding the polymer sheet, a uniform film of DLC will coat the surface of the sheet. The sheet can be used for growing many kinds of cells, and preferably neuronal cells, or as a vehicle for cell transplantation after sterilizing with UV radiation or 70% alcohol rinse.

Example 2

Coating of Biopolymer in the Form of Microparticles with DLC

The biopolymer microparticles will be placed into a specialized rotating chamber and a plume of carbon plasma is generated as previously described in Example 1. The plasma gun will introduce the spray of DLC into the chamber while it is rotated slowly in a vertical axis such that the microparticles will be tossed from top to bottom continuously so that the carbon plasma will have a chance to deposit on the entire surface area of each microsphere in a uniform manner. This process will be sustained over a period of about 2-3 hours to insure uniform and complete covering of all particle surfaces.

Example 3

Biopolymers with Attachment or Growth-Promoting Factors Embedded or Incorporated into its Composition During Synthesis and Subsequently Coated with DLC The biopolymer of the present invention can be embedded with, or incorporated into its composition during synthesis, attachment or growth promoting factors comprising of one or more of the following: fibronectin at concentrations ranging from 1 µg to 500 µg/ml of polymer gel, laminin at concentrations ranging from 1 µg to 500 µg/ml of polymer gel, RGDS at concentrations ranging from 0.1 µg to 100 µg/ml of polymer gel, bFGF conjugated with polycarbophil at concentrations ranging from 1 ng to 500 ng/ml of polymer gel, EGF conjugated with polycarbophil in concentrations ranging from 10 ng to 1000 ng/ml of polymer gel, NGF at concentrations of ranging from 1 ng to 1000 ng/ml of the polymer gel and heparin sulfate at concentrations ranging from 1 µg to 500 µg/ml of polymer gel. The biopolymer is then made into thin sheet or a semi-solid bloc, and DLC deposition can be achieved as previously described in Example 1. Or the polymer can be made into micro-particles or spheres, and DLC deposition can be achieved as previously described in Example 2.

Example 4

Coating of Biopolymer with Extracellular Matrix Deposited by Cultured Bovine Corneal Endothelial Cells and Subsequent Coating of the Sheet or Microparticles with DLC The biopolymer sheet, and block of microparticles can first be coated with an extracellular matrix (ECM) prior to the DLC deposition on the culture surface. To achieve this, bovine corneal endothelial cells (BCE) are seeded at low density (about 2000 to 150,000 cells/ml, preferably about 20,000 cells/ml) onto the surface of the sheet or block, or allowed to attach to the surface of the microparticles. The BCE cells are maintained in culture medium containing DME-H16 supplemented with 10% calf serum, 5% fetal calf serum, 2% Dextran (40,000 MV) and 50 ng/ml of bFGF. The cells are incubated at 37° C. in 10% $CO_2$ for 7 days, during which time bFGF at a concentration of 50 ng/ml is added every other day.

The BCE cells are removed by treating the polymer sheet, block, or microparticles with 20 mM ammonium hydroxide for 5 minutes. Then the biopolymer with the extracellular matrix coat is washed ten times with sufficient volume of PBS. After drying, the ECM coated polymer sheet or block is subjected to DLC deposition as previously described in Example 1, whereas the ECM-coated microparticles is subjected to DLC deposition as described in Example 2. After the sequential coating with ECM and DLC, the polymer sheet, block, or microparticle will be sterilized by UV irradiation or alcohol rinse, and used for neural cell growth or as a vehicle for cell transplantation.

Example 5

A Substrate Containing a Biopolymer Having Neurons Electrically Connected to an Integrated Circuit The biopolymer of the present invention can be embedded with, or incorporated into its composition during synthesis, attachment or growth promoting factors comprising of one or more of the following: fibronectin at concentrations ranging from 1 µg to 500 µg/ml of polymer gel, laminin at concentrations ranging from 1 µg to 500 µg/ml of polymer gel, RGDS at concentrations ranging from 0.1 µg to 100 µg/ml of polymer gel, bFGF conjugated with polycarbophil at concentrations ranging from 1 ng to 500 ng/ml of polymer gel, EGF conjugated with polycarbophil in concentrations ranging from 10 ng to 1000 ng/ml of polymer gel, NGF at concentrations of ranging from 1 ng to 1000 ng/ml of the polymer gel and heparin sulfate at concentrations ranging from 1 µg to 500 µg/ml of polymer gel. The biopolymer is then made into thin sheet or a semi-solid bloc, and DLC deposition can be achieved as previously described in Example 1. Or the polymer can be made into micro-particles or spheres, and DLC deposition can be achieved as previously described in Example 2.

On the DLC coated substrate, an integrated circuit or chip has been set in place. As described in Zeck, G. & Fromherz, Proc. Nat. Acad. Sci., 98, 10457-10462, (2001), nerve cells will be placed on a silicon chip with a DLC coating, and then the nerve cells are fenced in place with microscopic plastic pegs. Neighboring cells will grow connections with each other and with the chip. A stimulator beneath each nerve cell will create a change in voltage that will trigger an electrical impulse to travel through the cell. Electrical pulses applied to the chip will pass from one nerve cell to another, and back to the chip to trip a silicon switch.

Example 6

DLC Deposition on the Culture Surface of Tissue Culture Lab Ware

In the event of a flat culture surface such as a dish, filter insert, chamber slide, sheets, and blocks, the wares can be presented to the plasma gun with the culture surface-upwards in the vacuum chamber, and the coating process can proceed as previously described. In the case of the microcarrier beads, they need to be induced to flow in the chamber to insure uniform coating on all sides. For enclosed surfaces like flasks and tubes, a special modified plasma gun will be inserted into the vessel and coat the desired surface, A thin layer of DLC at the uniform thickness of about 20 to about 4000 Å, preferably about 200-400 Å will be deposited onto the culture surface. The products can then be sterilized by UV irradiation or alcohol rinsing, packaged, sealed, and stored on the shelf until use.

Example 7

Sequentially Coating the Culture Surface with ECM Secreted by Cultured Bovine Corneal Endothelial Cells and then DLC Deposition In this embodiment, sparse cultures (about 1000 to about 50,000 cells/ml, preferably 2000-5000 cells/ml) of bovine corneal endothelial cells are seeded onto the culture surface of the intended lab ware, which includes dishes, flasks, tubes, filter inserts, chamber slides, microcarrier beads, roller bottles, cell harvesters, sheets, and blocks. The cells are maintained in a medium containing DME-H16 supplemented with 10% calf serum, 5% fetal calf serum, 2% Dextran (40,000 MV), and bFGF at 50 ng/ml. The bovine corneal endothelial cells are grown for 7-10 days until confluence with bFGF added every other day at 50 ng/ml. Then the culture medium is removed and the cells are treated with sufficient 20 mM ammonium hydroxide in distilled water for 3 to 30 minutes. The surface is then washed with a sufficient amount of PBS 10 times to remove and residual ammonium hydroxide and dried in a sterile laminar flow hood. The coating of DLC can then be performed as previously described on top of the extracellular matrix. The product is then sterilized under UV radiation or alcohol rinse, and will be packaged, sealed, and stored on the shelf until use.

Example 8

Sequential Coating of the Culture Surface by Attachment or Growth Promoting Reagents Followed by DLC Deposit In this alternate embodiment, one or more of the attachment or growth promoting reagents comprised of fibronectin at concentrations ranging from 1 µg to 500 µg/ml, laminin at concentrations ranging from 1 µg to 500 µg/ml, RGDS at concentrations ranging from 0.1 µg to 100 µg/ml, bFGF conjugated with polycarbophil at concentrations ranging from 1 ng to 400 ng/ml, EGF conjugated with polycarbophil in concentrations ranging from 10 ng to 1000 ng/ml. The attachment or growth promoting reagents will be added to the culture surface, and then will be incubated at 4° C. for 20 minutes to 2 hours. The surface is then rinsed with PBS three times and dried in a sterile laminar flow hood. Then the product will be deposited with a DLC layer on top of the attachment or growth promoting reagent coat on the culture surface. The lab ware will then be sterilized by UV irradiation or alcohol rinse, packaged, sealed, and stored until use.

Having described the invention, many modifications thereto will become apparent to those skilled in the art to which it pertains without deviation from the spirit of the invention as defined by the scope of the appended claims.

The disclosures of U.S. Patents, patent applications, and all other references cited above are all hereby incorporated by reference into this specification as if fully set forth in its entirety.

4. The cell culture substrate of claim 1, wherein the biopolymer has embedded or incorporated into it during its synthesis one or more attachment reagents selected from the group consisting of: laminin, fibronectin, RGDS (SEQ ID NO: 1), basic fibroblast growth factor (bFGF) conjugated with polycarbophyll, epidermal growth factor (EGF) conjugated with polycarbophyll, and heparin sulfate.

5. A method of growing neurons in culture comprising:
providing the cell culture substrate of claim 1;
seeding neurons onto the hydrogen free diamond-like carbon; and
culturing the neurons.

6. The method of claim 5, wherein the biopolymer is in sheet form.

7. The method of claim 5, wherein the biopolymer is in micro particle form.

8. A method of growing neurons in culture comprising:
providing the cell culture substrate of claim 4;
seeding neurons onto the hydrogen free diamond-like carbon; and
culturing the neurons.

9. A three dimensional cell culture substrate comprising a semi-solid biopolymer coated with Diamond-Like Carbon, wherein the biopolymer is comprised of chitosan or sodium alginate, and wherein neural cells can attach to and grow on the surface of the Diamond-Like Carbon.

10. The cell culture substrate of claim 9, wherein the biopolymer has embedded or incorporated into it during its synthesis one or more attachment reagents selected from the group consisting of laminin, fibronectin, RGDS (SEQ ID NO: 1), basic fibroblast growth factor (bFGF) conjugated with polycarbophyll, epidermal growth factor (EGF) conjugated with polycarbophyll, heparin sulfate, and nerve growth factor (NGF), in an amount sufficient to allow neural or nerve cells transplanted onto the growth medium at low density to proliferate and send out neural processes.

11. The cell culture substrate of claim 10, wherein said biopolymer is shaped into beads, sheets or micro-particles.

The invention claimed is:

1. A cell culture substrate, comprising a biodegradable biopolymer coated with hydrogen free diamond-like carbon, wherein cells can attach to and grow on the surface of the hydrogen free diamond-like carbon.

2. The cell culture substrate of claim 1, wherein the biopolymer is in a sheet form.

3. The cell culture substrate of claim 1, wherein the biopolymer is in micro particle form.

12. A method of transplanting neurons to a recipient comprising:
providing the three dimensional cell culture substrate of claim 10;
seeding neurons of interest onto the diamond-like carbon;
allowing the neurons to grow to sufficient density; and
implanting the neurons on the cell culture substrate into said recipient.

13. A three dimensional cell culture substrate comprising a semi-solid biopolymer coated with bovine corneal epithelial cell-extracellular matrix (BCE-ECM) and the BCE-ECM is further coated with Diamond-Like Carbon, wherein neural cells can attach to and grow on the surface of the Diamond-Like Carbon.

14. The cell culture substrate of claim 13, wherein the biopolymer is comprised of chitosan or sodium alginate.

15. The cell culture substrate of claim 13, wherein the biopolymer has embedded or incorporated into it during its synthesis one or more attachment reagents selected from the group consisting of: laminin, fibronectin, RGDS (SEQ ID NO: 1), basic fibroblast growth factor (bFGF) conjugated with polycarbophyll, epidermal growth factor (EGF) conjugated with polycarbophyll, heparin sulfate, and nerve growth factor (NGF), in an amount sufficient to allow neural or nerve cells transplanted onto the substrate at low density to proliferate and send out neural processes.

16. The cell culture substrate of claim 15, wherein said biopolymer is shaped into beads, sheets or micro-particles.

17. A laboratory apparatus having a coating suitable for inducing the growth and attachment of cells, the apparatus having an inside and outside surface, wherein the inside surface is the surface in contact with cells and cellular media and the inside surface of said apparatus is coated with a film of Diamond-like-Carbon layered over a biopolymer coating.

18. The apparatus of claim 17, wherein the apparatus is selected from the group consisting of cell culture dishes, petri dishes, tissue culture flasks, plates, bottles, slides, filter chambers, slide chambers, roller bottles, harvesters and tubing.

19. A laboratory apparatus having a coating suitable for inducing the growth and attachment of cells, the apparatus having an inside surface and an outside surface, wherein the inside surface is the surface in contact with cells and cellular media and the inside surface of said apparatus is coated with a film of Diamond-like-Carbon, the Diamond-like-Carbon being layered over a biopolymer coating and at least one other coating.

20. The apparatus of claim 19, wherein the at least one other coating is an extracellular matrix.

21. The apparatus of claim 20, wherein the coating is BCE-ECM.

22. A method of making a laboratory apparatus suitable for inducing the growth and attachment of cells, the method comprising:
   a) obtaining a laboratory apparatus having an inside surface and an outside surface, wherein the inside surface is to be in contact with cells and cellular media;
   b) applying to the inside surface of the apparatus a biopolymer coating; then
   c) applying a film of Diamond-like-Carbon over the biopolymer coating.

23. The method of claim 22, further comprising between steps b) and c), step b') applying at least one other coating over the biopolymer coating.

\* \* \* \* \*

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<221> NAME/KEY: BINDING
<222> LOCATION:
<223> OTHER INFORMATION: Integrin binding peptide RGDS

<400> SEQUENCE: 1

Arg Lys Asp Ser
 1
```